(12) United States Patent
Olson

(10) Patent No.: US 10,363,042 B2
(45) Date of Patent: *Jul. 30, 2019

(54) TILTING ANVIL FOR ANNULAR SURGICAL STAPLER

(71) Applicant: Covidien LP, Mansfield, MA (US)

(72) Inventor: Lee Ann Olson, Wallingford, CT (US)

(73) Assignee: Covidien LP, Mansfield, MA (US)

(*) Notice: Subject to any disclaimer, the term of this patent is extended or adjusted under 35 U.S.C. 154(b) by 373 days.

This patent is subject to a terminal disclaimer.

(21) Appl. No.: 15/272,509

(22) Filed: Sep. 22, 2016

(65) Prior Publication Data

US 2017/0007256 A1 Jan. 12, 2017

Related U.S. Application Data

(63) Continuation of application No. 13/950,635, filed on Jul. 25, 2013, now Pat. No. 9,451,962, which is a continuation of application No. 13/030,683, filed on Feb. 18, 2011, now Pat. No. 8,496,157.

(51) Int. Cl.
*A61B 17/115* (2006.01)
*A61B 17/072* (2006.01)

(52) U.S. Cl.
CPC .... *A61B 17/1155* (2013.01); *A61B 17/07207* (2013.01); *A61B 2017/07257* (2013.01)

(58) Field of Classification Search
CPC .......... A61B 17/1155; A61B 17/07207; A61B 17/068
USPC .......................... 227/19, 175.1, 176.1, 180.1
See application file for complete search history.

(56) References Cited

U.S. PATENT DOCUMENTS

| | | | |
|---|---|---|---|
| 4,379,457 A | 4/1983 | Gravener et al. |
| 4,527,724 A | 7/1985 | Chow et al. |
| 4,892,244 A | 1/1990 | Fox et al. |
| 4,893,622 A | 1/1990 | Green et al. |
| 4,903,697 A | 2/1990 | Resnick et al. |
| 5,005,749 A | 4/1991 | Aranyi |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,292,053 A | 3/1994 | Bilotti et al. |

(Continued)

FOREIGN PATENT DOCUMENTS

| | | |
|---|---|---|
| CA | 2416508 A1 | 7/2004 |
| EP | 0570915 A2 | 11/1993 |

(Continued)

OTHER PUBLICATIONS

European Search Report dated Feb. 10, 2017, issued in European Application No. 16183122.

(Continued)

*Primary Examiner* — Nathaniel C Chukwurah

(57) ABSTRACT

A surgical stapling instrument is disclosed, the instrument having a handle assembly, a body portion having a staple cartridge assembly, and an anvil assembly. The anvil assembly includes an anvil head, an anvil member, an anvil shaft, and a biasing member. The anvil shaft defines a longitudinal axis and the anvil member is pivotally secured to the anvil head. The biasing member is supported on the anvil assembly to urge the anvil member from a first position to a second position defining an angle with respect to the longitudinal axis.

10 Claims, 3 Drawing Sheets

(56) References Cited

U.S. PATENT DOCUMENTS

| | | |
|---|---|---|
| 5,333,773 A | 8/1994 | Main et al. |
| 5,350,104 A | 9/1994 | Main et al. |
| 5,403,312 A | 4/1995 | Yates et al. |
| 5,443,198 A | 8/1995 | Viola et al. |
| 5,464,144 A | 11/1995 | Guy et al. |
| 5,474,223 A | 12/1995 | Viola et al. |
| 5,487,499 A | 1/1996 | Sorrentino et al. |
| 5,503,320 A | 4/1996 | Webster et al. |
| 5,529,235 A | 6/1996 | Boiarski et al. |
| 5,533,661 A | 7/1996 | Main et al. |
| 5,535,935 A | 7/1996 | Vidal et al. |
| 5,535,937 A | 7/1996 | Boiarski et al. |
| 5,588,579 A | 12/1996 | Schnut et al. |
| 5,607,436 A | 3/1997 | Pratt et al. |
| 5,639,008 A | 6/1997 | Gallagher et al. |
| 5,685,474 A | 11/1997 | Seeber |
| 5,688,270 A | 11/1997 | Yates et al. |
| 5,697,543 A | 12/1997 | Burdorff |
| 5,709,680 A | 1/1998 | Yates et al. |
| 5,758,814 A | 6/1998 | Gallagher et al. |
| 5,762,255 A | 6/1998 | Chrisman et al. |
| 5,797,537 A | 8/1998 | Oberlin et al. |
| 5,799,857 A | 9/1998 | Robertson et al. |
| 5,807,393 A | 9/1998 | Williamson, IV et al. |
| 5,810,811 A | 9/1998 | Yates et al. |
| 5,820,009 A | 10/1998 | Melling et al. |
| 5,833,690 A | 11/1998 | Yates et al. |
| 5,882,340 A | 3/1999 | Yoon |
| 5,915,616 A | 6/1999 | Viola et al. |
| 6,010,054 A | 1/2000 | Johnson et al. |
| 6,024,741 A | 2/2000 | Williamson, IV et al. |
| 6,050,472 A | 4/2000 | Shibata |
| 6,053,390 A | 4/2000 | Green et al. |
| 6,066,145 A | 5/2000 | Wurster |
| H1904 H | 10/2000 | Yates et al. |
| 6,258,107 B1 | 7/2001 | Balazs et al. |
| 6,269,997 B1 | 8/2001 | Balazs et al. |
| 6,601,748 B1 | 8/2003 | Fung et al. |
| 6,769,594 B2 | 8/2004 | Orban, III |
| 6,945,444 B2 | 9/2005 | Gresham et al. |
| 6,957,758 B2 | 10/2005 | Aranyi |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,179,267 B2 | 2/2007 | Nolan et al. |
| 7,234,624 B2 | 6/2007 | Gresham et al. |
| 7,237,708 B1 | 7/2007 | Guy et al. |
| 7,303,106 B2 | 12/2007 | Milliman et al. |
| 7,325,713 B2 | 2/2008 | Aranyi |
| 7,364,060 B2 | 4/2008 | Milliman |
| 7,364,061 B2 | 4/2008 | Swayze et al. |
| 7,431,191 B2 | 10/2008 | Milliman |
| 7,464,847 B2 | 12/2008 | Viola et al. |
| 7,494,038 B2 | 2/2009 | Milliman |
| 7,516,877 B2 | 4/2009 | Aranyi |
| 7,546,940 B2 | 6/2009 | Milliman et al. |
| 7,556,186 B2 | 7/2009 | Milliman |
| 7,766,210 B2 | 8/2010 | Shelton, IV et al. |
| 7,770,775 B2 | 8/2010 | Shelton, IV et al. |
| 7,802,712 B2 | 9/2010 | Milliman et al. |
| 7,810,692 B2 | 10/2010 | Hall et al. |
| 7,845,534 B2 | 12/2010 | Viola et al. |
| 7,845,537 B2 | 12/2010 | Shelton, IV et al. |
| 7,857,187 B2 | 12/2010 | Milliman |
| 7,870,989 B2 | 1/2011 | Viola et al. |
| 8,141,763 B2 | 3/2012 | Milliman |
| 8,496,157 B2 * | 7/2013 | Olson ............... A61B 17/1155 227/176.1 |
| 9,451,962 B2 | 9/2016 | Olson |
| 2004/0195289 A1 | 10/2004 | Aranyi |
| 2005/0006432 A1 | 1/2005 | Racenet et al. |
| 2005/0006433 A1 | 1/2005 | Milliman et al. |
| 2005/0023325 A1 | 2/2005 | Gresham et al. |
| 2005/0067457 A1 | 3/2005 | Shelton et al. |
| 2005/0067458 A1 | 3/2005 | Swayze et al. |
| 2005/0103819 A1 | 5/2005 | Racenet et al. |
| 2005/0116009 A1 | 6/2005 | Milliman |
| 2005/0205639 A1 | 9/2005 | Milliman |
| 2005/0205640 A1 | 9/2005 | Milliman |
| 2006/0025816 A1 | 2/2006 | Shelton |
| 2006/0097025 A1 | 5/2006 | Milliman et al. |
| 2006/0175375 A1 | 8/2006 | Shelton et al. |
| 2006/0212069 A1 | 9/2006 | Shelton |
| 2006/0219752 A1 | 10/2006 | Arad et al. |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0278680 A1 | 12/2006 | Viola et al. |
| 2007/0034670 A1 | 2/2007 | Racenet et al. |
| 2007/0060952 A1 | 3/2007 | Roby et al. |
| 2007/0075117 A1 | 4/2007 | Milliman et al. |
| 2007/0078486 A1 | 4/2007 | Milliman et al. |
| 2007/0108252 A1 | 5/2007 | Racenet et al. |
| 2007/0175964 A1 | 8/2007 | Shelton et al. |
| 2007/0272722 A1 | 11/2007 | Aranyi |
| 2008/0142566 A1 | 6/2008 | Gresham et al. |
| 2008/0230581 A1 | 9/2008 | Marczyk et al. |
| 2009/0179063 A1 | 7/2009 | Milliman et al. |
| 2009/0250502 A1 | 10/2009 | Milliman |
| 2010/0038401 A1 | 2/2010 | Milliman et al. |
| 2010/0200635 A1 | 8/2010 | Milliman |
| 2010/0327041 A1 | 12/2010 | Milliman et al. |
| 2011/0152861 A1 | 6/2011 | Weisshaupt et al. |
| 2012/0234891 A1 | 9/2012 | Aronhalt et al. |
| 2012/0234892 A1 | 9/2012 | Aronhalt et al. |

FOREIGN PATENT DOCUMENTS

| | | |
|---|---|---|
| EP | 0639349 A2 | 2/1995 |
| EP | 0698376 A2 | 2/1996 |
| EP | 1658813 A1 | 5/2006 |
| EP | 1857058 A1 | 11/2007 |
| EP | 2335608 A2 | 6/2011 |
| WO | 0166020 A2 | 9/2001 |
| WO | 2007014513 A1 | 2/2007 |

OTHER PUBLICATIONS

Canadian Office Action dated Feb. 9, 2018, issued in Canadian Application No. 2,765,548.
U.S. Pat. No. 5,826,777, Oct. 1998, Green et al. (withdrawn).
European Search Report EP 12 15 5873.
Australian Examiner's Report dated Jul. 16, 2015 in connection with corresponding Australian Patent Application No. 2012200343.

* cited by examiner

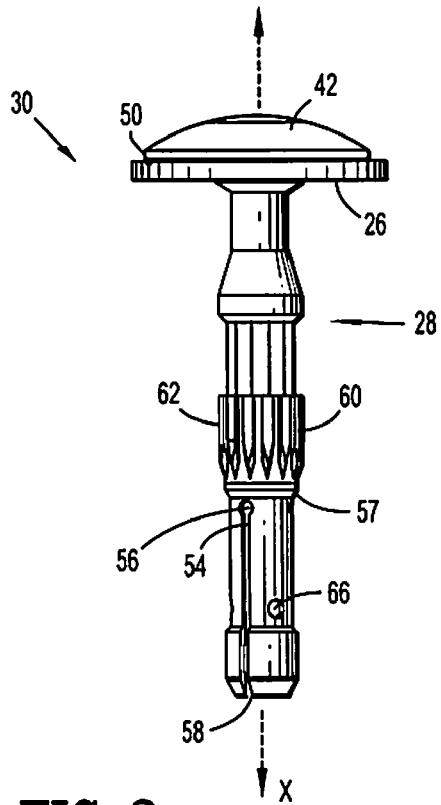
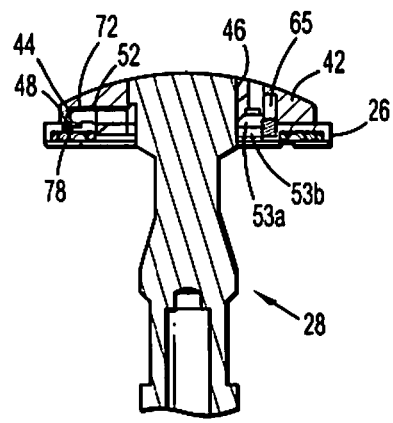
FIG. 3
FIG. 2
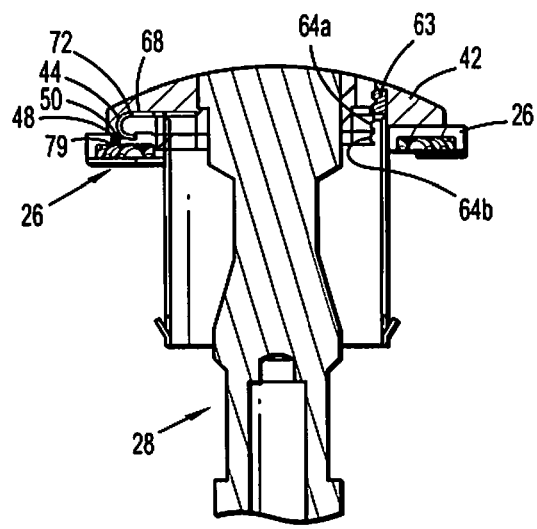
FIG. 4

TILTING ANVIL FOR ANNULAR SURGICAL STAPLER

CROSS-REFERENCE TO RELATED APPLICATION

The present application is a continuation of U.S. patent application Ser. No. 13/950,635, filed Jul. 25, 2013, (now U.S. Pat. No. 9,451,962) which is a continuation of U.S. patent application Ser. No. 13/030,683 filed Feb. 18, 2011, (now U.S. Pat. No. 8,496,157) the content of each is incorporated herein by reference in its entirety.

TECHNICAL FIELD

The present disclosure relates to a surgical stapling instrument having an anvil that tilts with respect to the shaft of the anvil assembly. More particularly, the anvil member has a pivotable connection with the anvil assembly.

BACKGROUND OF RELATED ART

Anastomosis is the surgical joining of separate hollow organ sections to allow the sections to communicate with each other. An anastomosis can follow a procedure in which a section of hollow tissue is removed, such as a section of the intestine, and the remaining end sections are to be joined. Depending on the desired anastomosis procedure, the end sections may be joined end-to-end or side-to-side, for example.

Circular surgical stapler instruments that perform an anastomosis procedure are known. The instrument joins two ends of the organ sections by driving a circular array of staples through the organ sections and cutting the tissue to form a tubular passage. The instrument includes an actuating handle assembly and a tubular body portion extending therefrom. The body portion receives a staple cartridge assembly and has a shaft that connects to an anvil assembly. Retraction of the shaft clamps tissue between the anvil assembly and the staple cartridge assembly. Staples are driven into staple receiving recesses and the tissue is cut by a circular knife. See U.S. Pat. No. 5,443,198 to Viola et al., the entire disclosure of which is hereby incorporated by reference herein.

After the staples have been fired, the entire instrument must be removed from the site. The anvil assembly has a rigid anvil head and has a profile that can make it difficult to remove the instrument from the tubular organ.

In order to reduce the transverse profile of the anvil assembly during placement and removal of the anvil assembly from a hollow organ, anvil assemblies having a tiltable anvil head have been developed. One such anvil assembly is described in U.S. Pat. No. 6,053,390, filed on May 10, 1999, which is hereby incorporated by reference herein, in its entirety. The pivotable anvil head is normally locked in the operative firing position. Upon firing the stapling device, the lock is released and the anvil head moves to a position that is tilted with respect to the shaft.

A need still exists for an improved surgical stapling instrument having an anvil assembly that minimizes the difficulties associated with removing the instrument after it has been fired, and that is easier to deliver into hollow tissues to be joined.

SUMMARY

According to an aspect of the present disclosure, a surgical stapling instrument, comprising a handle assembly a body portion extending from the handle assembly, and an anvil assembly is disclosed. The body portion has a rod and a staple cartridge assembly. The staple cartridge assembly defines staple receiving slots. The anvil assembly includes an anvil head, an anvil member, an anvil shaft, and a biasing member. The anvil shaft defines a longitudinal axis and is connectable to the rod. The anvil member is pivotally secured to the anvil head about a transverse axis, the transverse axis being transverse to the longitudinal axis. The anvil member defines staple forming recesses. The biasing member is supported on the anvil assembly to urge the anvil member from a first position to a second position defining an angle with respect to the longitudinal axis.

In certain embodiments, the anvil member is urged from the first position and pivots about the transverse axis to the second position. The anvil assembly may include a pivot member for pivotally securing the anvil member to the anvil head.

In certain embodiments, the anvil head has an inner recess and a cutting ring disposed in the inner recess. A movable connector is releasably connected to the cutting ring. The movable connector is connected to the anvil member and movable with respect to the anvil head. The surgical stapling instrument has a knife movable into the movable connector, and the movable connector is moved out of engagement with the anvil member by the knife.

The cutting ring may have a circular groove and the movable connector may have a circular shape, the circular shape of the movable connector being engageable with the circular groove of the cutting ring.

In certain embodiments, the anvil head has a notch for retaining the biasing member. The biasing member may comprise a spring. The spring has one end that engages the anvil head and another end that engages the anvil member. The surgical stapling instrument can include a first cutting ring and a second cutting ring disposed in an inner recess of the anvil head.

BRIEF DESCRIPTION OF THE DRAWINGS

The accompanying drawings which are incorporated in and form a part of this specification, illustrate embodiments of the present disclosure and, together with a general description above, and the detailed description of the embodiments given below, serve to explain the principles of this disclosure, wherein:

FIG. 2 is an elevation view of an anvil assembly in accordance with the embodiment of FIG. 1 showing the anvil member in an initial position;

FIG. 3 is an elevation view of the anvil assembly, shown in section, in accordance with the embodiment of FIGS. 1 and 2;

FIG. 4 is an elevation view of the anvil assembly, shown in section, in accordance with the embodiment of FIGS. 1 through 3;

DETAILED DESCRIPTION OF PREFERRED EMBODIMENTS

Figure 1:
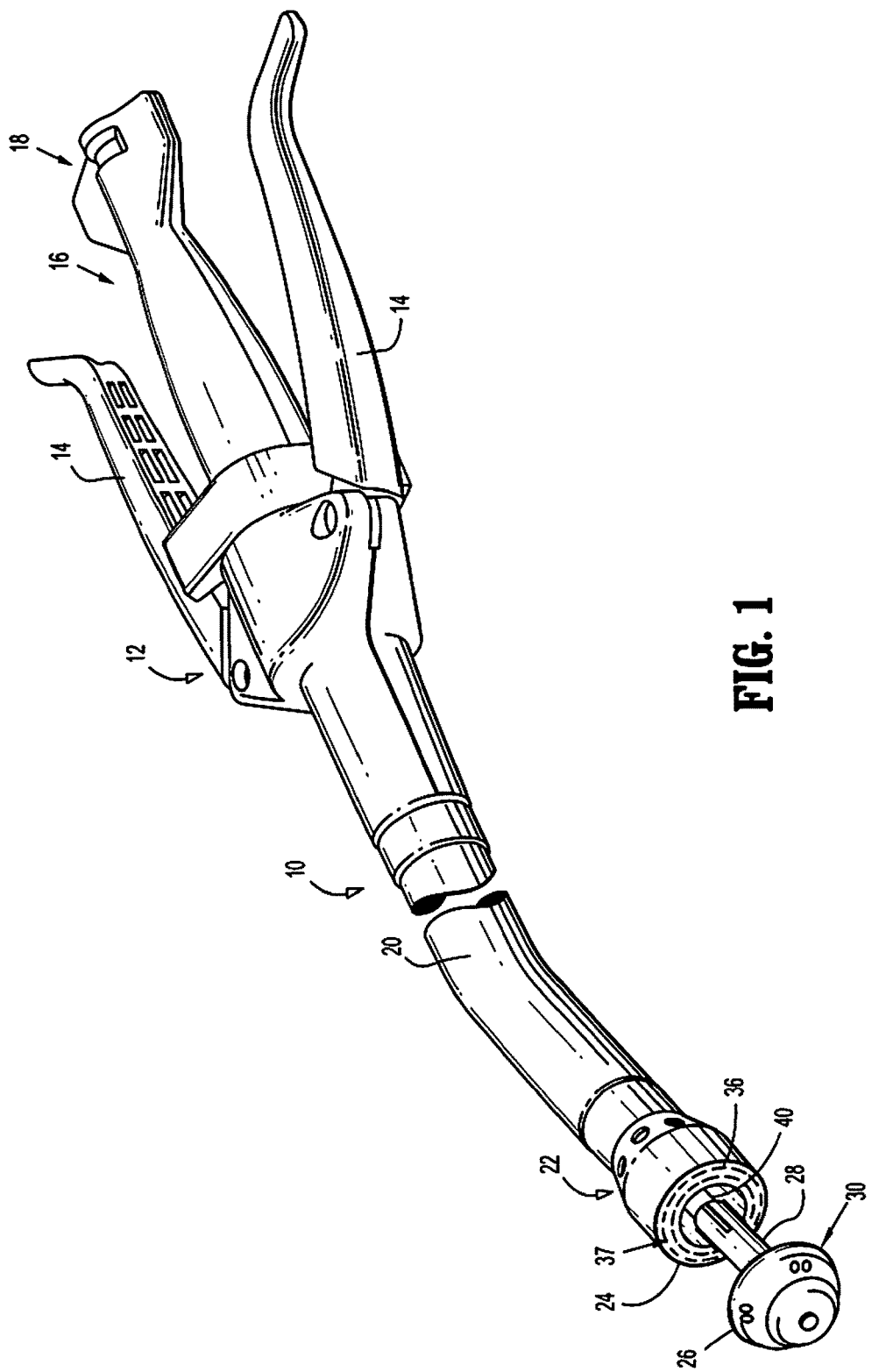
FIG. 1 is a perspective view of a surgical stapling instrument in accordance with an embodiment of the present disclosure.

Preferred embodiments of the presently disclosed instrument will now be described in detail with reference to the drawings in which like reference numerals designate identical or corresponding elements in each of the several views. The term "proximal," as is customary, refers to a position closer to the surgeon, whereas the term "distal" refers to a position farther away from the surgeon.

FIG. 1 illustrates a circular surgical stapling instrument which is generally designated as 10. Surgical stapling instrument 10 includes a handle assembly 12 having at least one pivotable actuating handle 14 and a rotatable actuator 18. A tubular body portion 20 extends from the handle assembly 12. The tubular body portion 20, which generally has a circular cross-sectional shape, may have a straight or a curved shape along its length and may be flexible or relatively rigid. Cross-sectional shapes other than circular are contemplated, so that the tubular body portion 20 can have a polygonal, elliptical, semi-circular, ovoid, or other shape. The body portion 20 terminates in a staple cartridge assembly 22 which includes a distally facing tissue contacting surface defining one or more rows 37 of staple receiving slots 36. Each staple receiving slot has a staple (not shown) disposed therein. Typically, a pair of circular rows 37 of staple receiving slots 36 is provided, although other shapes, such as annular, are contemplated. An anvil assembly 30 is positioned distally of the staple cartridge assembly 22, which includes an anvil member 26 and an anvil shaft 28 operatively associated therewith. The anvil assembly has a proximally facing tissue contacting surface that defines staple forming recesses that correspond to the circular rows of staple receiving slots. The tubular body portion 20 has a corresponding rod or shaft 40 centrally located with respect to the staple cartridge assembly 22. The shaft 28 of the anvil assembly is removably connectable to the rod or shaft 40 of the tubular body portion 20. The anvil shaft defines a longitudinal axis "x".

The staple cartridge assembly 22 is connectable to the distal end of tubular body portion 20 or may be configured to concentrically fit within the distal end of tubular body portion 20. Typically, staple cartridge assembly 22 includes a staple pusher (not shown) with a distal portion defining two concentric rings of peripherally spaced fingers (not shown), each one of which is received within a respective staple receiving slot 36. Typically, the knife (not shown) having a cutting edge is disposed within the staple cartridge assembly 22. The knife edge is circular and disposed radially inward of the rows of staples. The knife is mounted so that as the staple pusher is advanced axially in the direction of the anvil assembly, the knife is also advanced axially. The staple pusher is advanced in the distal direction to drive staples from the staple receiving slots 36 against the anvil member so that the staple forming recesses form the staples in a closed shape. As the pusher is advanced, the knife is advanced and driven toward the anvil assembly 30 to cut tissue. U.S. Pat. No. 5,915,616 to Viola et al., the entire content of which is incorporated herein by reference, discloses a circular stapling instrument. Although a circular stapling instrument is shown in FIG. 1, the stapling device may be arranged to deploy staples in a semi-circular or other desired shape. Although discussed with reference to intestinal tissue, devices according to the present disclosure can be arranged to join and/or treat other tissues in other procedures.

Figure 5:
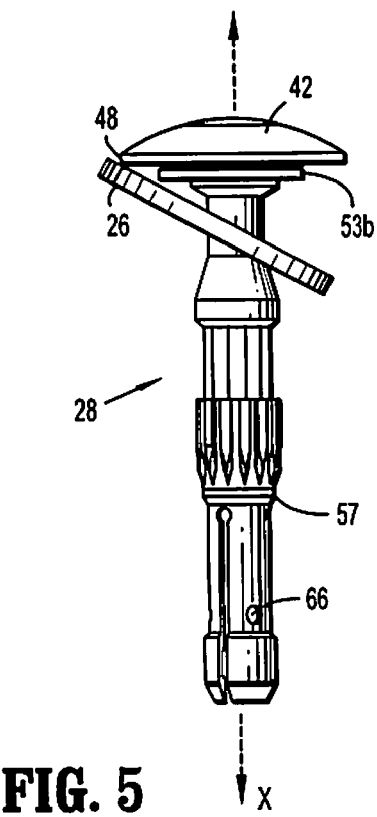
FIG. 5 is an elevation view of an anvil assembly in accordance with the embodiment of FIGS. 1 through 4, showing the anvil member in another position.
Figure 6:
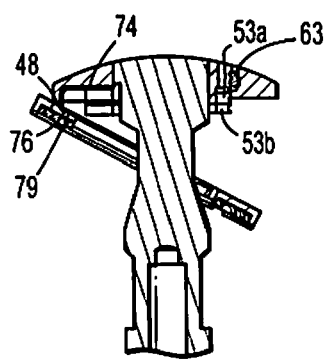
FIG. 6 is an elevation view of the anvil assembly, shown in section and with the anvil member in another position, in accordance with the embodiment of FIGS. 1 through 5.

Referring to FIGS. 2 and 3, the anvil assembly 30 includes an anvil head 42, an anvil member 26, an anvil shaft 28, and a biasing member 44. The anvil head 42 includes a centrally located through bore 46 dimensioned to receive anvil shaft 28. The anvil member 26 is pivotably connected to the anvil head 42 by a pivot member 48. The pivot member 48 defines an axis transverse to the longitudinal axis "x". The pivot member 48 includes a pin or post which defines transverse axis 50 which is transverse to, and spaced laterally from, the longitudinal "x" axis of anvil shaft 28. The anvil member 26 can pivot about the pivot member 48 from a first, initial position (FIG. 2) in which a plane defined by the tissue contacting surface of the anvil member 26 is substantially perpendicular to the longitudinal axis of anvil shaft 28 to a second position, tilted with respect to the longitudinal axis "x". The second position is desirably a reduced profile position (FIGS. 5 and 6) in which anvil member 26 defines an angle with respect to the longitudinal axis "x". Alternately, other types of pivot members at different locations in relation to the axis "x" of the anvil shaft may be incorporated into the anvil assembly.

The anvil shaft 28 includes a passage 54 having a first end 56 and a second end 58. In certain preferred embodiments, the first end 56 includes at least one bore 66 dimensioned to receive a suture or the like to facilitate positioning of anvil assembly 30 within a hollow organ.

The anvil shaft 28 is dimensioned to releasably engage an anvil retainer (not shown) on the rod or shaft 40 of a circular surgical stapling instrument, such as the surgical stapling instrument 10. One such surgical stapling device having an anvil retainer and with which anvil assembly 30 may be used is disclosed in U.S. provisional patent application Ser. No. 60/281,259, filed Apr. 3, 2001, ("the '259 application") which is hereby incorporated by reference herein, in its entirety. The anvil shaft 28 includes a projection 57, which may be annular in shape, and which is dimensioned to lockingly engage the anvil retainer. The anvil assembly includes a guide collar 60, which may be monolithically formed with the anvil shaft 28. Alternately, the guide collar 60 may include a sleeve separate from the anvil shaft 28. Guide collar 60 includes circumferentially spaced splines 62 which function to align anvil assembly 30 with the body portion 20 (FIG. 1) of the surgical stapling instrument 10 during movement of the anvil assembly 30 from a positioned spaced from the staple cartridge assembly 22 of the surgical stapling device to an approximated position in close alignment with the staple cartridge assembly 22.

In certain embodiments, the anvil head 42 has an inner recess 52 that is generally annular in shape and configured to receive a first upper cutting ring 53a and a second lower cut ring 53b. The cutting ring 53a and cutting ring 53b are each generally annular or circular in shape, having a central opening for accommodating the anvil shaft 28. Alternatively, one or more than two cutting rings can be utilized. The cutting ring 53a and cutting ring 53b are formed with one or more grooves 64 that correspond to the shape of a movable connector or snap member 63. The movable connector is releasably connected to the cutting ring, is also connected to the anvil head, and is movable with respect to the anvil head. The movable connector 63 has a first portion that engages the cutting ring and a second portion that engages the anvil member 26. The movable connector has inwardly facing circular shapes that face toward the axis "x". In the embodiment shown, the cutting ring 53a and cutting ring 53b have outwardly-facing circular grooves 64a and 64b that engage the similar circular shapes on the movable connector 63. The inner recess 52 further defines a space 65 above the movable connector 63, and the movable connector is movable in the upward direction, from an initial position in which the movable connector 63 engages the cutting ring 53a, cutting ring 53b, and the anvil member 26, to another position that is disengaged from the anvil member 26. Preferably, the movable connector 63 is attached to, or retained in, the anvil head 42 when disengaged from the anvil member 26.

The inner recess 52 of the anvil head 42 also defines a notch 68 for retaining a biasing member 44. The biasing member 44 can be, for example, a spring 72 that has one end 74 that engages the anvil head 42 in the recess 52, and another end 76 that engages a surface 78 on the anvil member 26. A ridge or protrusion 79 can be provided in the anvil head to help retain the spring 72. The biasing member 44 can also be, in other embodiments, a resilient piece of material or pad that presses onto the surface 78. In other embodiments, the biasing member 44 is an electronic component with a movable actuator that pushes against the surface 78, or otherwise acts on the surface 78, such as a micro electromechanical unit with a mechanical actuator.

In use, as discussed above, the anvil assembly 30 is secured to the surgical stapling instrument 10 by connecting the anvil shaft 28 to the rod 40. The actuator 28 is rotated by the user, which withdraws the rod 40 and anvil shaft 28 so that the anvil assembly 30 is approximated with the staple cartridge assembly 22 to clamp tissue. The user of the instrument then manipulates handle 14 to fire the staples and cut the tissue. As the knife is advanced, the knife contacts the movable connector 63, pushing it into the anvil head 42, disengaging the movable connector 63 from the anvil member 26. With the movable connector disengaged from the anvil member, the anvil member is free to pivot about the pivot member 48 under the influence of the biasing member 44. The anvil member pivots from the first initial position to the second tilted position. In the second position, the anvil member defines an angle with respect to the longitudinal axis "x". In certain preferred embodiments, the pivot member 48 and/or anvil member 26 are configured so that the anvil member 26 pivots to a position that eases the removal of the anvil assembly 30 from the tissue. The tilting feature also allows the anvil to tilt over and around the donut-shaped tissue that is created after the tissue is cut and not pinch the tissue under the head of the anvil assembly. See FIGS. 5 and 6. Preferably, the upper and lower cutting rings 53a and 53b are retained in the anvil head 42 or on the anvil shaft 28 after the instrument has been fired.

The above-described surgical stapling instrument and anvil assembly may be used in gastro-intestinal procedures. A gastric bypass procedure is described in PCT application Ser. No. PCT/US01/07105, filed Mar. 5, 2001, and U.S. Provisional patent application Ser. No. 60/187,121, filed Mar. 6, 2000, both of which are incorporated herein in their entirety by reference. Alternately, the above described anvil assembly may be used in other surgical procedures especially those in which a reduced profile anvil assembly is desirable.

It will be understood that various modifications may be made to the embodiments disclosed herein. For example, the movable connector may engage the anvil member and the anvil shaft. In other embodiments, the biasing member may be connected to the anvil shaft. Therefore, the above description should not be construed as limiting, but merely as exemplifications of preferred embodiments. Those skilled in the art will envision other modifications within the scope and spirit of the claims appended hereto.

What is claimed is:

1. An anvil assembly comprising:
   an anvil shaft having proximal and distal portions and defining a longitudinal axis, the proximal portion being configured for releasable connection with an actuation device;
   an anvil head secured to the distal portion of the anvil shaft; and
   an anvil member pivotally connected to the anvil head and having a tissue contacting surface that defines staple forming recesses, the anvil member being pivotable about an axis that is laterally spaced from and transverse to the longitudinal axis of the anvil shaft from a first position in which the tissue contacting surface is perpendicular to the longitudinal axis and a second position in which the tissue contacting surface is at an angle relative to the longitudinal axis.

2. The anvil assembly according to claim 1, further including a connector disposed within the anvil head, wherein the connector is movable from an initial position in engagement with the anvil member to secure the anvil member in the first position, to a subsequent position disengaged from the anvil member to permit pivoting of the anvil member to the second position.

3. The anvil assembly of claim 2, further including a biasing member positioned to urge the anvil member from the first position towards the second position.

4. The anvil assembly of claim 3, wherein the anvil head defines a notch configured to retaining the biasing member within the anvil head.

5. The anvil assembly of claim 4, wherein the biasing member includes a spring.

6. The anvil assembly of claim 5, wherein a first end of the spring engages the anvil head and a second end of the spring engages the anvil member.

7. The anvil assembly of claim 2, wherein the anvil head defines an inner recess for receiving the connector.

8. The anvil assembly of claim 7, wherein the connector is movable within the inner recess from the initial position in engagement with the anvil member to the position disengaged from the anvil member.

9. The anvil assembly of claim 8, further including a cutting ring supported within the anvil head, wherein the connector includes a first portion configured to engage the cutting ring and a second portion configured to engage the anvil member.

10. The anvil assembly of claim 1, wherein in the first position the anvil member defines a first cross-sectional area, and in the second position, the anvil member defines a second cross-sectional area, the first cross-sectional area being larger than the second cross-sectional area.

* * * * *